United States Patent [19]

Carr

[11] 4,346,716

[45] Aug. 31, 1982

[54] MICROWAVE DETECTION SYSTEM

[75] Inventor: Kenneth L. Carr, Harvard, Mass.

[73] Assignee: M/A COM, Inc., Burlington, Mass.

[21] Appl. No.: 135,506

[22] Filed: Mar. 31, 1980

[51] Int. Cl.³ ............................................. A61B 5/05
[52] U.S. Cl. .................... 128/653; 128/736; 128/804
[58] Field of Search ......................... 128/736, 653, 804

[56] References Cited

U.S. PATENT DOCUMENTS

| | | | |
|---|---|---|---|
| 2,407,690 | 9/1946 | Southworth | 128/804 |
| 3,065,752 | 11/1962 | Pötzl | 128/804 |
| 3,810,459 | 5/1974 | Becker | 128/663 |
| 4,138,998 | 2/1979 | Nowogrodzki | 128/736 |

FOREIGN PATENT DOCUMENTS

| | | | |
|---|---|---|---|
| 2815156 | 10/1978 | Fed. Rep. of Germany | 128/804 |
| 862646 | 3/1961 | United Kingdom | 128/804 |

OTHER PUBLICATIONS

Sterzer, F., "Apparatus for Hyperthermia Treatment", PCT GB 2000335 A (UK Patent Appl.) 4 Jan. 1979.
Larsen, L. et al., "A Microwave De Coupled Brain Temperature Transducer", IEEE Trans. on Microwave Theory & Techniques, vol. MTT-22, No. 4, pp. 438-444 Apr. 1974.
Barrett, A. H. et al., "Sub-Cutoneous Temps: A Method of Non-Invasive Sensing", Science vol. 190, Nov. 1975, pp. 669-671.
Griffin, D. W., "MW Interferometers for Biological Studies", Microwave Jrnl., vol. 21, May 1978, pp. 69-71.
Lenox, R. H. "A Microwave Applicator for In Vivo Rapid Inactivation of Enzymes in the Central Nervous System", IEEE Trans. on M-wave Theory & Tech. vol. MTT-24 #1, pp. 58-61, Jan. 1976.

Primary Examiner—Kyle L. Howell
Assistant Examiner—Francis J. Jaworski
Attorney, Agent, or Firm—Wolf, Greenfield & Sacks

[57] ABSTRACT

The microwave system is employed for the detection of cancerous tumors and is particularly effective in the early detection of such tumors. The system is of the dual type, combining in a single unit a passive radiometer with an active microwave transmitter. The sensitive passive microwave radiometer is adapted to sense subsurface temperatures, coupled with a solid state microwave transmitter for providing localized heating of the subsurface tissue, thereby taking advantage of the differential heating due to vascular insufficiency associated with the thermal characteristics of tumors, thus highlighting and enhancing early detection of cancer. The radiometer frequency is preferably higher than the microwave heating frequency with the microwave radiometer operating in C band and the transmitter in L band. An applicator forms the means by which the system couples to the radiating or emitting surface including a simple $TE_{1-0}$ mode aperture defined by a single-ridged waveguide.

19 Claims, 7 Drawing Figures

MICROWAVE DETECTION SYSTEM

BACKGROUND OF THE INVENTION

The present invention relates in general to an improved passive microwave detection technique for early detection of cancerous tumors. More particularly, the invention relates to a system adapted to provide localized heating of subsurface tissue with the use of an active microwave transmitter in combination with a passive radiometer for detecting a temperature differential occasioned by the differential heating between the tumor and adjacent tissue.

Studies have been conducted on the ability to measure temperature gradients particularly deep within the body tissue in connection with clinical medicine and research. For example, see the articles to A. H. Barrett, P. C. Myers and N. L. Sadowsky, "Detection of Breast Cancer by Microwave Radiometry." *Radio Science* 12, No. 6(S), 167, 1977; Ronald A. Porter and Harry H. Miller, "Microwave Radiometric Detection and Location of Breast Cancer." (Preprint.); J. Bigu del Blanco and C. Romero-Sierra, "MW Radiometry: A New Technique to Investigate the Interaction of MW Radiation with Living Systems." 27th ACEMB, Philadelphia, Pa., Oct. 6-10, 1974. These temperature gradients occur, it is theorized, because of vascular insufficiency associated with the thermal characteristics of tumors. It is well known that a carcinoma or malignant tumor is normally hotter than the surrounding tissue. It is also known that, from "black body" theory, any perfectly absorbing body emits radiation at all frequencies in accordance with Planck's radiation law. A recent article on the differential heating characteristics is one by B. C. Giovanella, "Correlation of Thermosensitivity of Cells to Their Malignant Potential." Conference on Thermal Characteristics of Tumors: Applications in Detection and Treatment; New York Academy of Sciences, Mar. 15, 1979.

The application of thermal therapy (i.e., localized heating) has been used to reduce tumor size or to even destroy the tumor. It has been found that tumor temperatures greater than 45° C. can be maintained with the normal tissue adjacent to the tumor at the same time remaining at or near normal body temperature. It has been reported by several investigators that cell tumor tissue will necrose at temperatures above 42° C. See the articles by David N. Leff, "Hyperthermia-Hottest News in Cancer Therapy." *Medical World News*, May 14, 1979; Jozef Mendecki, Esther Friedenthal and Charles Botstein, "Effects of Microwave-induced Local Hyperthermia on Mammary Adenocarcinoma in C3H Mice." Cancer Research 36, 2113–2114, June 1976; James Schaeffer, "Treatment of Metastatic Osteogenic Sarcoma in Mice with Whole Body Hyperthermia and/or Irradiation." International Symposium on Cancer Therapy by Hyperthermia and Radiation, Washington, D.C., 1975. Thermal therapy used in conjunction with other conventional techniques involving drugs or radiation has proven to be effective (i.e., anti-cancer drugs act more effectively at elevated temperatures and, similarly, permit lower level X-ray treatment). The combination of microwave detection with infra red detection is reported by Barrett and Myer, supra.

In accordance with the present invention, there is provided a sensitive microwave radiometer technique for sensing subsurface temperatures wherein the technique is not invasive. It has been common in the past to employ a conventional thermistor probe inserted in the area of the tumor, and studies have been made with regard to the effect on the heating patterns induced by microwave diathermy apparatus. See the Articles by Thomas C. Cetas, "Temperature Measurements in Microwave Diathermy Fields: Principles and Probes." International Symposium on Cancer Therapy by Hyperthermia and Radiation, Washington, D.C., 1975; Len Yencharis, "Temperature Probe Designed For Cancer Therapy." *Electronic Engineering Times*, 18, Jan. 9, 1978. The results of these studies indicate that the heating pattern is altered considerably by the presence of the sensor.

The microwave radiometer of the present invention is in effect a very sensitive radio receiver capable of measuring temperature differentials down to 0.1° C. or less. The receiver, when provided with a highly directional antenna and technique of observation, provides a reading of power picked up by the antenna. As mentioned previously, any perfectly absorbing body emits radiation at all frequencies in accordance with Planck's radiation law. The distribution of radiation is a function of both the temperature and wavelength or frequency. As the temperature of the body increases, the density of the radiation at all frequencies also increases. From this viewpoint, infra red thermography or radiometry, appears to be effective, however, the depth of penetration (depth of effective emission) becomes a limiting factor. The highest value of radiation density occurs in the optical region. Nevertheless, an appreciable amount of radiation exists at the microwave segment of the spectrum. In accordance with the present invention the power accepted in a known bandwidth by an antenna having defined characteristics can be accurately computed as a function of the temperature of the emitter.

As mentioned previously, a carcinoma or malignant tumor normally radiates more heat than the surrounding tissue. See the article by R. N. Lawson and M. S. Chughtai, "Breast Cancer and Body Temperature." Canadian Medical Association, Vol. 88, Jan. 12, 1963. Early detection, namely detection prior to invasion or metastases, requires the detection of tumors less than five millimeters in diameter with an associated temperature deviation of less than 0.2° C. It has been found in accordance with the techniques of this invention that such early detection is quite accurate, and that tumors of relatively small size can be detected which heretofore have not been capable of detection by such conventional techniques as X-ray mammography.

Accordingly, one of the objects of the present invention is to provide an improved technique for the diagnosis and treatment of cancer employing a non-invasive microwave detection system.

Another object of the present invention is to provide in a single unit the combination of both a microwave transmitter or source and a passive detector or microwave radiometer.

A further object of the present invention is to provide a microwave system employing a sensitive passive microwave radiometer particularly adapted for sensing subsurface temperatures in combination with a solid state microwave transmitter for providing localized heating of subsurface tissue. With such a combined system, there is essentially a highlighting of the tumor to enhance detection, thus taking advantage of the differential heating characteristics of the tumor with respect to the surrounding tissue.

Still another object of the present invention is to provide an improved microwave system for the early detection of cancer and which is adapted for use, not only for detection purposes but also for treatment purposes.

Still a further object of the present invention is to provide a microwave system for cancer diagnosis which is totally battery operated to thus eliminate possible problems associated with line transients and the like.

Another object of the present invention is to provide an improved microwave system for the detection of cancerous tumors and which is non-invasive, thus, not requiring the use of any temperature sensing probes. The present invention employs a sensitive passive microwave radiometer particularly designed to sense subsurface temperatures.

Still another object of the present invention is to provide an improved microwave system for the detection of cancerous tumors and which is capable of sensing at a temperature resolution down to at least 0.1° C.

A further object of the present invention is to provide an improved microwave system for the detection of cancerous tumors and which is particularly adapted for the detection of relatively newly-formed tumors of extremely small size.

Another object of the present invention is to provide, in a microwave system, an improved, extremely sensitive passive radiometer capable of measurements of temperature deviations even less than 0.1° C.

SUMMARY OF THE INVENTION

To accomplish the foregoing and other objects of this invention, there is provided in accordance with the present invention, a microwave system for the diagnosis of cancerous tumors employing non-invasive microwave techniques. This system may also be employed in the treatment of cancer. The system is preferably totally battery operated, thus eliminating any possible problems associated with line transients, pickup, etc. The system comprises a sensitive passive microwave radiometer particularly adapted for sensing subsurface temperatures, in combination with a solid state transmitter that provides localized heating of the subsurface tissue. This localized heating essentially enhances the tumor from a temperature differential standpoint, taking advantage of the differential heating due to vascular insufficiency associated with the thermal characteristics of tumors. This technique highlights and enhances the early detection of cancer tumors. The selection of both the radiometer and the transmitter frequencies is based upon the following factors:

1. Emissivity, which increases with increasing frequency;
2. Spatial resolution; and
3. Microwave transmission characteristics.

In the embodiment disclosed herein, the frequency for the radiometer is selected at 4.7 GHz sufficiently removed from the selected microwave heating frequency of 1.6 GHz.

An applicator forms the means by which the system couples to the body. This applicator employs a simple $TE_{1-0}$ mode aperture that is placed in direct contact with the radiating or emitting surface. The aperture is formed by a single-ridged waveguide which is preferred because its use lowers the frequency at which cutoff occurs. To further reduce the size of the aperture, dielectric loading is employed. The waveguide dimensions for operation at L-band and the dimensions of the ridged portion of the L-band ridged wave guide are selected to allow propagation of the higher frequency associated with the C-band radiometer. By having the radiometer input contained within the single-ridged waveguide L-band transition, the point of maximum field of the source of the heat is in close proximity with the area of thermal detection. The cut-off characteristics of the C-band waveguide are utilized in addition to other filtering that is provided; the waveguide forming a high pass filter to isolate the high power L-band source from the sensitive radiometer. A heater and proportional thermostat are provided in the dual mode transition or antenna (applicator) to maintain a constant temperature at or very near to the temperature of the human body.

Another advantage of the system of this invention is that when the applicator is uncoupled from the human body, the level of radiation is very small and well within safety standards. This advantage is realized by the large mismatch associated with the low impedance ridged waveguide when left open-circuited. When so removed, there is a mismatch with the atmosphere which has a low dielectric constant. The measured radiation level one inch from the waveguide opening with the L-band source fully operating is well within safety standards. For example, one power measurement was less than 0.4 mW/sq. cm. The safety standard established by the federal government is 10 mW/sq. cm.

BRIEF DESCRIPTION OF THE DRAWINGS

Numerous other objects, features and advantages of the invention should now become apparent upon a reading of the following detailed description taken in conjunction with the accompanying drawings in which.

DETAILED DESCRIPTION

The microwave system of this invention comprises an extremely sensitive passive radiometer capable of measurements of temperature deviations of less than 0.1° C. The dual mode microwave system also employs a solid state transmitter to provide localized heating of the cancer site. In the particular arrangement described herein, the C-band radiometer frequency is 4.7 GHz and the L-band transmitter frequency is 1.6 GHz. The system also includes a dual mode antenna comprising a C-band aperture in combination with an L-band applicator. The microwave transmitter causes an elevation of the temperature of the tumor above that of the surrounding normal tissue to thus enhance the detection by highlighting the tumor with respect to the surrounding or background tissue. The heating of the cancer site results in a differential heating of the tumor with respect to the surrounding tissue. Also, because temperatures above about 42° C. are lethal to tumor cells, the system is also applicable for the treatment of cancer.

As mentioned previously, the system is preferably totally battery operated, allowing approximately 8 hours of continuous service prior to requiring a recharging. Such a battery operated system is employed as it eliminates possible problems associated with line transients, pickup, etc. A battery charging circuit is included in the system with an overnight charging cycle being designed to provide the batteries in a fully charged condition for the next day's use. Three sealed, maintenance free, lead acid batteries are connected in series, providing a maximum voltage of 36 volts.

Figure 1:
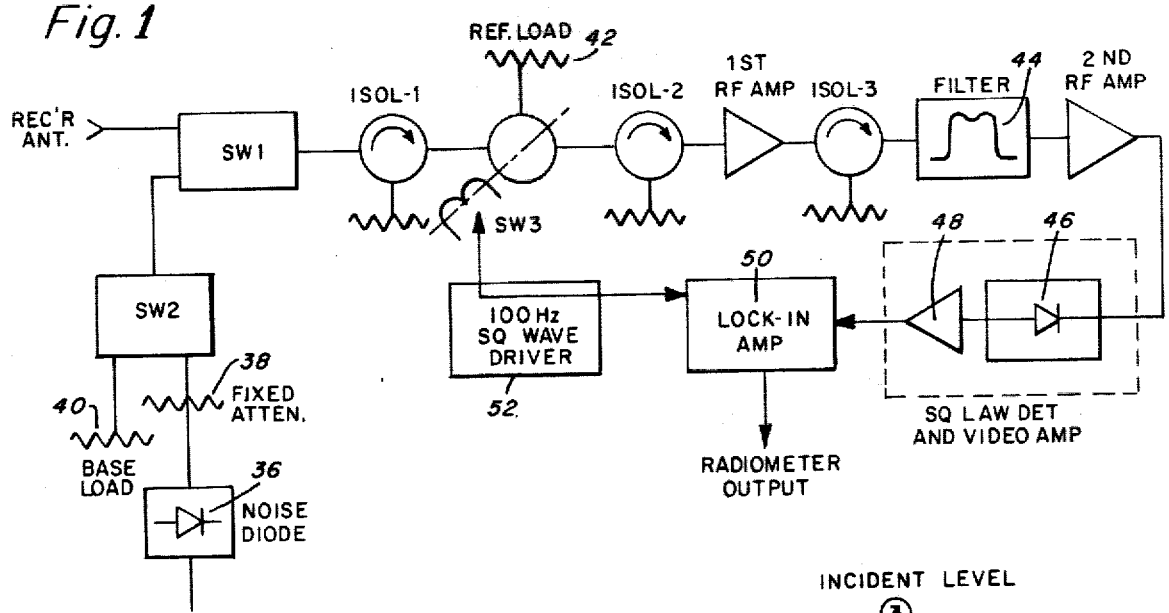
FIG. 1 is a schematic diagram of the microwave radiometer employed in the system of this invention.
Figure 2:
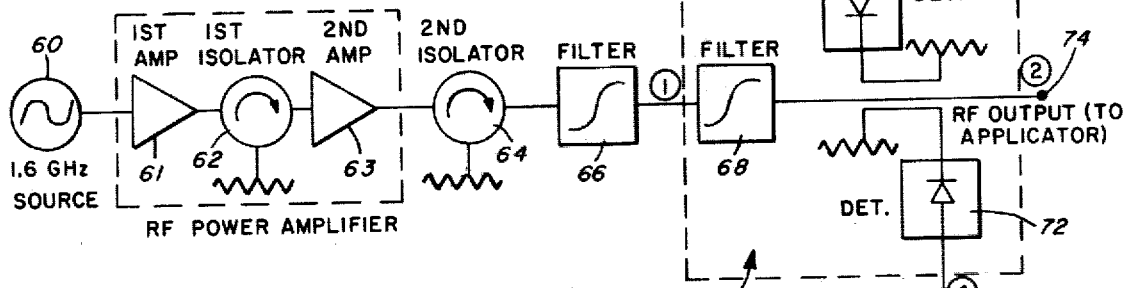
FIG. 2 is a schematic diagram of the L-band transmitter employed in the system.

FIG. 1 is a schematic diagram of the microwave radiometer of this invention. FIG. 2 shows a schematic diagram of the transmitter employed in this system. The radiometer and transmitter both couple to the dual mode antenna with the radiometer receiving its signal from the C-band aperture and the transmitter directing its signal to the L-band applicator. Accordingly, a discussion of the dual mode antenna receives a discussion hereinafter of the radiometer and transmitter schematic diagrams.

As previously mentioned, the frequency selected for localized heating is 1.6 GHz. For this frequency, a normal waveguide transition that would be used would have dimensions of 5.100″ (12.95 cm)×2.550″ (6.48 cm). These dimensions correspond to a WR-510 guide. Thus, to reduce the physical size of the applicator aperture a single ridged waveguide construction is used. The use of a ridged waveguide lowers the cutoff frequency allowing use at a lower operating frequency or, in the present situation, allowing the use of a smaller aperture size. To further reduce the overall size of the aperture, dielectric loading is employed. The dielectric that is utilized is preferably aluminum oxide having a relative dielectric constant, $e_r$, of 9.8. With the utilization of both a ridged waveguide and dielectric loading the aperture size is substantially reduced with respect to the tumor thus providing greater resolution and improved focusing.

Figure 4:
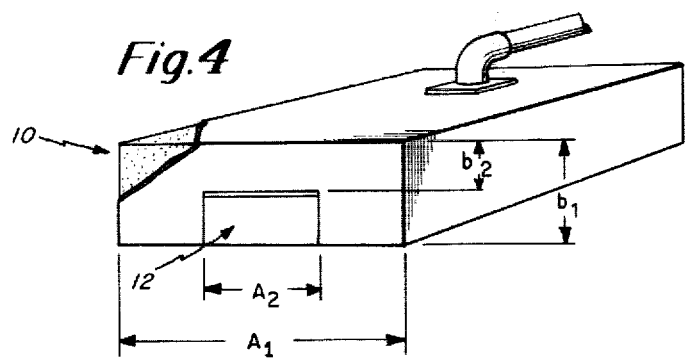
FIG. 4 is a perspective view of the dual mode antenna and waveguide construction.
Figure 5:
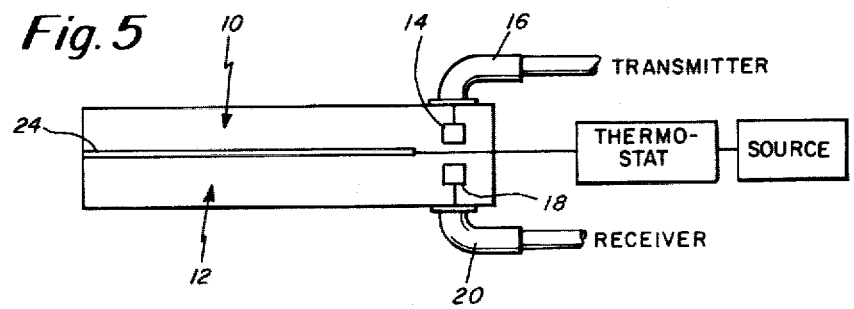
FIG. 5 is a side view of the waveguide construction depicted in FIG. 4.

FIGS. 4 and 5 show the dual mode antenna construction which comprises an L-band applicator 10 and a C-band aperture 12. The applicator 10, as noted in the drawing, is in the form of a single ridge waveguide. This waveguide receives a signal from the probe 14 which couples in turn to the coax line 16. Similarly, there is provided a probe 18 associated with the C-band aperture 12 coupling to an associated coax line 20.

The ridged waveguide dimensions as identified in FIG. 4, are as follows:

$A_1 = 9.296$ cm $A_2 = 4.648$ cm $b_1 = 4.648$ cm $b_2 = 2.154$ cm reduced due to dielectric loading, $e_r = 9.8$, to $A_1 = 3.66$ cm $A_2 = 1.83$ cm $b_1 = 1.83$ $b_2 = 0.85$ The following calculated parameters apply, namely $\lambda g$ guide wavelength = 26.63 cm
$\lambda o$ free space wavelength = 18.64 cm
$\lambda c$ cutoff wavelength = 27.89 cm
$Zo\infty$ characteristic impedance at an infinite frequency = 150 ohms
$Zo$ characteristic impedance = 214 ohms For a calculation of these parameters see Samuel Hopfer, "The Design of Ridged Waveguides." IRE Trans., Vol. MTT-3, No. 5; October 1955 and S. B. Cohn, "Properties of Ridged Waveguide." Proc. IRE, Vol. 35, pp. 783-788; August 1947.

The insertion loss may be obtained by measuring the total loss of two identical transitions in series (i.e., mated at the waveguide opening). Assuming the two transitions to be equal in loss, the single transition loss is 0.2 dB maximum. The VSWR, when held against the human body was approximately 1.5:1. Since the human body does not represent a fixed termination but rather a variable match, a reflectometer is included at the transmitter output to enable determination of the reflected and incident power levels. Both of these measured levels may be easily combined to provide a single output reading.

The dimensions of the ridged portion of the L-band ridged waveguide are selected to allow propagation of the higher frequency associated with the C-band radiometer. As indicated in FIG. 4, the C-band transition or aperture has dimensions of a height of 0.92 centimeters and a width of 1.83 centimeters.

The plated surfaces of the dielectric-loaded C-band waveguide form and coincide with the single ridge of the L-band waveguide as depicted in FIG. 4. The plating may be of nickel, copper or gold, for example. With regard to the C-band aperture, the insertion loss is measured to be less than 0.3 dB. The VSWR, when held against the human body is less than 2:1.

By placing the radiometer input within the single ridged waveguide L-band transition, the point of maximum field of the source of heat is in close proximity with the point of thermal detection. The cutoff characteristics of the C-band waveguide are used along with other filtering to form a highpass filter for isolating the highpower L-band source from the sensitive radiometer.

Figure 3:
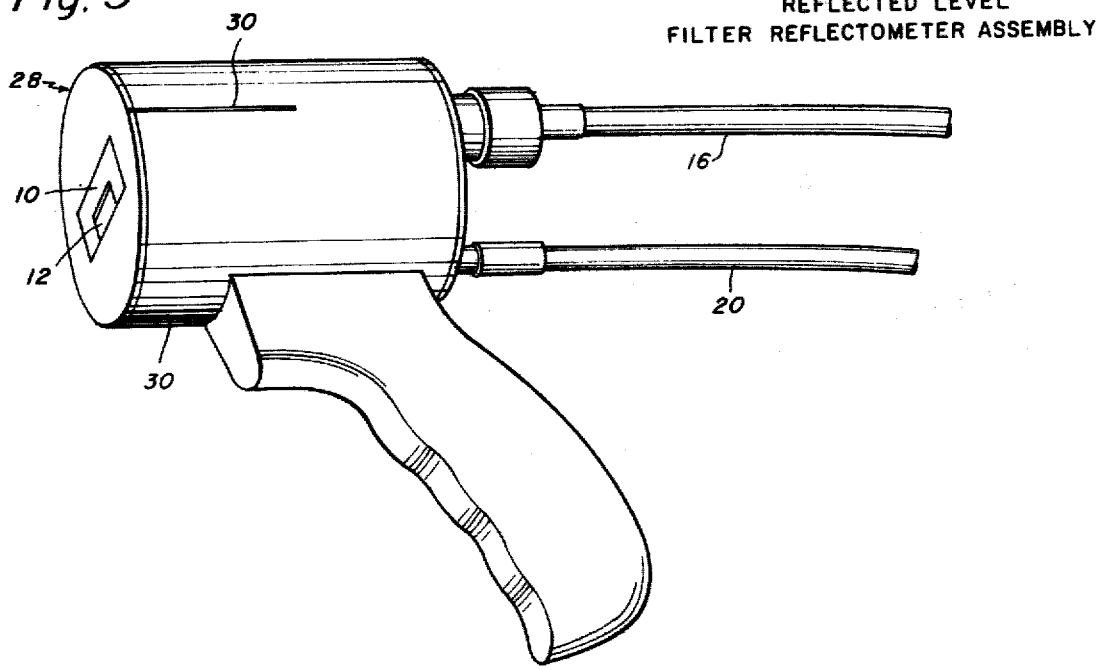
FIG. 3 shows the body transition element in the form of a hand-held applicator.

As indicated in FIGS. 4 and 5, and in particular in FIG. 5, there is provided a heater 24 which is disposed between the applicator and the aperture. This heater may be of conventional design and is in the form of a thin sheet having associated therewith a proportional thermostat for maintaining a constant temperature at or very near to that of the temperature of the human body. The microwave assembly is then contained in an insulated housing 28 having indexing lines 30 on the outer surface as shown in FIG. 3. The indexing lines are located 90° apart on the perimeter of the housing to allow accurate positioning of the C-band radiometer input. To allow accurate and repeatable positioning of the antenna, an indexed silk screen and frame (not shown) may be provided. The use of the tightly drawn silk screen allows flattening of the portion of the body to be scanned. The mismatch and loss associated with this thin silk screen is negligible.

The microwave system of this invention is also quite safe to use. One of the characteristics of the system is that there is a large mismatch on the order of 12:1 associated with the low impedance ridged waveguide when left open circuited. (i.e., in the atmosphere removed from the human body with its high dielectric constant to which the waveguide is matched). Utilizing a Narda Model No. 8607 power meter placed within one inch from the waveguide opening with the L-band power source fully on, the measured level was less than 0.4 mW/cm². The safety standard established by the government is 10 mW/cm² for electromagnetic radiation, regardless of frequency. For example, microwave ovens are permitted to radiate at a level of 5 mW/cm² at a distance of 2" from the oven.

Referring now to FIG. 1, there is shown a schematic diagram of the microwave radiometer showing the signal coupled from the receiver antenna (C-band aperture) to the switch SW1. The microwave radiometer that is depicted is of special design in accordance with the present invention but is generally of the common load comparison, or Dicke, type. The radiometer design substantially reduces the effects of short term gain fluctuations in the radiometer. The receiver input is switched by means of switch SW1 at a constant rate between the antenna and a constant temperature reference load. The switched, or modulated RF signal is therefore inserted at a point prior to RF amplification and as close to the antenna as possible; in turn, it is then amplified and coherently detected. The final output is proportional to the temperature difference between the antenna and the reference load.

In FIG. 1 a second switch SW2, referred to as a calibration switch, is also employed. With this switch, the reference load as defined by the noise diode 36 and the fixed attenuator 38, is compared with a base load 40 rather than the signal from the antenna. If the base load is equal in temperature with the reference load, the DC output of the radiometer is thus nulled to zero.

In the case where long integration times are involved, long term gain variations in the receiver are considered. The long term, or slow, gain variations can degrade the minimum detectable temperature sensitivity, ΔT, in accordance with the following expression:

$$\Delta T \text{ variation (due to long term gain change)} = \frac{\Delta G}{G} \mid T_1 - T_2 \mid, °K.$$

where ΔG = receiver gain change
G = nominal receiver gain
$T_1$ = temperature of reference load °K.
$T_2$ = temperature of base load or antenna, °K. (function of calibration switch position)

If the temperature $T_1$ and $T_2$ are maintained approximately the same, the effect of long term receiver gain variations becomes negligible. Therefore, it is advantageous to maintain the temperatures of both the base load 40 and the reference load 42 approximately equal to the temperature of the antenna.

The radiometer described herein employs at least one low noise RF amplifier in conjunction with a simple single-ended square law detector rather than the more complex superheterodyne which employs a local oscillator and IF amplifier. The square law detector of this arrangement minimizes the potential drift and noise associated with the superheterodyne approach. The components that comprise the radiometer are discussed in detail hereinafter.

Associated with FIG. 1 is table I set out herein which lists the individual components shown in FIG. 1 along with their identifying part number and brief description of their purpose or function.

TABLE I

| ITEM | PART NO. | PURPOSE OR FUNCTION |
|---|---|---|
| RECEIVER ANTENNA | MA-56825 | COAX-TO-WAVEGUIDE TRANSITION - INTEGRATED WITH TRANSMITTER ANTENNA |
| SWITCH-1 | MA-56829 | SPDT COAXIAL MECHANICAL SWITCH - GREATER THAN 60 dB ISOLATION; LESS THAN 0.1 dB LOSS |
| ISOLATOR-1 | MA-56831 | STRIPLINE FERRITE ISOLATOR WITH INTEGRATED STRIPLINE-TO-WAVEGUIDE TRANSITION |
| ISOLATOR-2 | MA-56834 | WAVEGUIDE FERRITE ISOLATOR WITH INTEGRATED TRANSITION TO COAX |
| SWITCH-3 | MA-56832 | WAVEGUIDE FERRITE ISOLATOR SWITCH - DICKE SWITCH |
| REFERENCE LOAD 42 | MA-56836 | REFERENCE LOAD - COAXIAL TERMINATION WITH INTEGRATED HEATER AND PROPORTIONAL CONTROL |
| BASE LOAD 40 | MA-56836 | BASE LOAD - COAXIAL TERMINATION WITH INTEGRATED HEATER AND PROPORTIONAL CONTROL |
| FIRST RF AMPLIFIER | AMPLICA MODEL 3131CS1 | RF AMPLIFIER (FET) HAVING 2.2 dB NOISE FIGURE AND 35 dB GAIN |
| ISOLATOR-3 | MA-56837 | COAXIAL FERRITE ISOLATOR - 20 dB MINIMUM ISOLATOR WITH LESS THAN 0.3 dB LOSS |
| FILTER 44 | MA-56838 | STRIPLINE BANDPASS FILTER - 500 MHz BANDWIDTH |
| SECOND RF AMPLIFIER | AMPLICA MODEL 3441CS | RF AMPLIFIER (FET) HAVING 2.6 dB NOISE FIGURE AND 33 dB GAIN |
| SQUARE LAW DETECTOR AND VIDEO AMPLIFIER | MA-56841 | FIRST RF DETECTION HAVING 20 dB VIDEO GAIN |
| LOCK-IN AMPLIFIER 50 | PRINCETON APPLIED RESEARCH MODEL | PROVIDES IMPROVED SIGNAL-TO-NOISE RATIO THROUGH FREQUENCY LOCK AND NARROW BANDWIDTH - PROVIDES SYNCHRONOUS |

TABLE I-continued

| ITEM | PART NO. | PURPOSE OR FUNCTION |
|---|---|---|
| | 5101 | DETECTION |
| SWITCH-2 | MA-56829 | SPDT COAXIAL MECHANICAL SWITCH PROVIDING GREATER THAN 60 dB ISOLATION AND LESS THAN 0.1 dB LOSS |
| NOISE DIODE 36 | MSC MODEL MC5048 | NOISE SOURCE - 30 dB EXCESS NOISE |
| FERRITE SWITCH DRIVER/56 | MA-56839 | PROVIDES 100 Hz SQUARE WAVE REFERENCE TO LOCK-IN AMPLIFIER ALSO PROVIDES LATCHING FERRITE SWITCH DRIVE. |

The minimum detectable temperature sensitivity, $\Delta T$ is expressed as follows:

$$\Delta T = \frac{k\,[(FL-1)\,T_1 + T_2]}{\sqrt{B\tau}}, \,°K.$$

In the case of the Dicke switch employing square wave modulation, the value of k is 2.0.

F = noise figure (first amplifier stage), which in our case is 2.2 dB (1.66 ratio).
L = input losses, expressed as a power ratio. The total loss is 2.0 dB (1.58 ratio).
The effective noise figure, FL, is therefore 2.2+2, or 4.2, which represents a power ratio of 2.63.
$T_1$, is the ambient radiometer temperature (microwave portion), namely, 290° K.
$T_2$, the source temperature (i.e., temperature seen by antenna), namely 310° K.
B, the receiver bandwidth (i.e., the 3 dB bandwidth of the bandpass filter following the first RF amplifier); namely, 500 MHz.
$\tau$, the radiometer output time constant in seconds.

Utilizing a three-second time constant, there is a minimum detectable temperature sensitivity of:

$$\Delta T = \frac{2\,[(2.63-1)\,290 + 310]}{\sqrt{500 \times 10^6 \times 3}}, \text{ or } .04° \text{ K. rms}$$

Increasing the time constant, T, to 10 seconds results in a $\Delta T$ of 0.02° K. Similarly, reducing the time constant to one second results in a $\Delta T$ of 0.07° K.

The signal level at the input to the square law detector 46 of FIG. 1 is determined as follows:

Noise Temp., $NT = (FL-1)T_o$, °K.
F = noise figure (first amplifier stage), which in our case is 2.2 dB (1.66 ratio).
L = input losses, expressed as a power ratio.
$T_o$ = ambient temperature of the radiometer, °K.

The losses at 4.7 GHz, prior to the amplifier, are as follows:

| Antenna or Applicator | 0.3 dB |
|---|---|
| Cable | 0.7 |
| Calibration Switch SW1 | 0.1 |
| Isolator/Waveguide Adapter | 0.3 |
| Dicke Switch SW3 | 0.3 |
| Ferrite Isolator | 0.2 |
| Waveguide-to-Coax Adapter | 0.1 |
| | 2.0 dB (1.58 ratio) |

The effective noise figure, FL, is therefore 2.2+2, or 4.2 dB, which represents a power ratio of 2.63.

$NT = (2.63-1)290 = 473° K.$

To calculate the noise power at the input to the radiometer, we have $P_N = kTB$ watts
$k$, = Boltzmann's constant = $1.38 \times 10^{-23}$ µjoules/°K.
T = 473° K. (calculated above)
B = bandwidth of radiometer, Hz; namely, 500 MHz (equivalent to the 3 dB bandwidth of the bandpass filter)
$P_N = 1.38 \times 10^{-23} \times 473 \times 500 \times 10^6 3.26 \times 10^{-12}$ watts Converting dB, we have $$10 \log (3.26 \times 10^{-12}) =$$
$$= 5.13 - 120 =$$
$$-114.87 \, dB,$$
$$\text{or } -84.87 \, dbm =$$

The combined amplifier gain less the loss of the bandpass filter is 64 dB, resulting in an input level to the square wave detector of $(-84.9 + 64)$ or $-20.9$ dbm which is well within the square law region.

With regard to the microwave radiometer schematic of FIG. 1, at its input there is shown the connection which is preferably by way of a coax cable from the receiver antenna (applicator aperture) to one input of switch SW1. This may be termed a calibration switch which is a solenoid-operated, mechanical, single pole/double-throw switch used to disconnect the antenna and in its place connect the base load 40 by way of a second switch SW2. The switch SW1 has an isolation, or switching ratio, of greater than 60 dB with a corresponding insertion loss of less than 0.1 dB. The switch SW2 is used in the calibration circuit to disconnect the base load and to insert in its place the calibrated noise source as represented by the fixed attenuator 38 and the noise diode 36 referred to hereinafter.

As indicated in FIG. 1, there are three ferrite isolators used in the receiver path. These are identified as isolators ISOL-1, ISOL-2 and ISOL-3. The first isolator, is located between the calibration switch SW1 and the Dicke switch SW3. This isolator is used to terminate the output of the reference load when the Dicke switch is in the low loss state. In this state, the reference or base load is circulated in the direction of the antenna which, in this case, functions as a ferrite isolator. The isolator ISOL-1 employs a coaxial-to-waveguide transition. The insertion loss of this isolator and the transition is less than 0.2 dB, with a corresponding isolation of greater than 23 dB.

The second isolator ISOL-2 in FIG. 1, is disposed between the switch SW3 and the first stage RF amplifier to maintain a constant load match to this amplifier. Any reflections from the RF amplifier would therefore be terminated in the isolator. Again, this isolator, which is a waveguide isolator with a coax-to-waveguide transition, has an insertion loss of less than 0.2 dB with an isolation of greater than 23 dB.

There is also provided in FIG. 1 a third isolator ISOL-3 which is located between the output of the first RF amplifier and the bandpass filter 44. The purpose of this particular isolator is to present a constant load match to the output stage of the first RF amplifier, and also to present a matched input to the bandpass filter 44.

A switchable ferrite circulator, designated switch SW3 in FIG. 1, forms the load comparison, or Dicke switch, function. A ferrite device is preferred over a semi-conductor approach primarily in view of the lower insertion loss, typically less than 0.3 dB, and elimination of noise generated by the semi-conductor junction over and above the measured insertion loss.

Briefly, the device SW3 is a switchable ferrite junction circulator utilizing the remnant, or latching, characteristics of the ferrite material. The principle of latching action is as follows: Using the intrinsic properties of a hysterisis loop of a ferrite toroid, a transverse magnetic field is used across a portion of the ferrite exposed to an RF signal. The biasing field is actually the residual inductance of the ferrite toroid; therefore, the device needs no holding power and can be reversed in polarity using merely enough energy to overcome the natural coercive force of the toroid.

For the system of this invention, the latching circulator has been constructed in waveguide having a single ferrite element contained within the microwave circuit. The insertion loss is less than 0.3 dB, having isolation in excess of 20 dB.

The first-stage RF amplifier may be a four stage FET device constructed in microstrip with integrated biasing circuitry. The noise figure of the first amplifier (Amplica Model No. 3131CSI) is 2.2 dB with a gain of 35 dB. The second RF amplifier (Amplica Model No. 3441CS) has a noise figure of 2.6 dB, with an associated gain of 33 dB. In both instances, the noise figure includes the input ferrite isolator as depicted in FIG. 1. With the input and output VSWR at less than 1.5:1, the gain compression at signal levels of between $-55$ dbm to $-10$ dbm is less than 0.1 dB.

Figure 6:
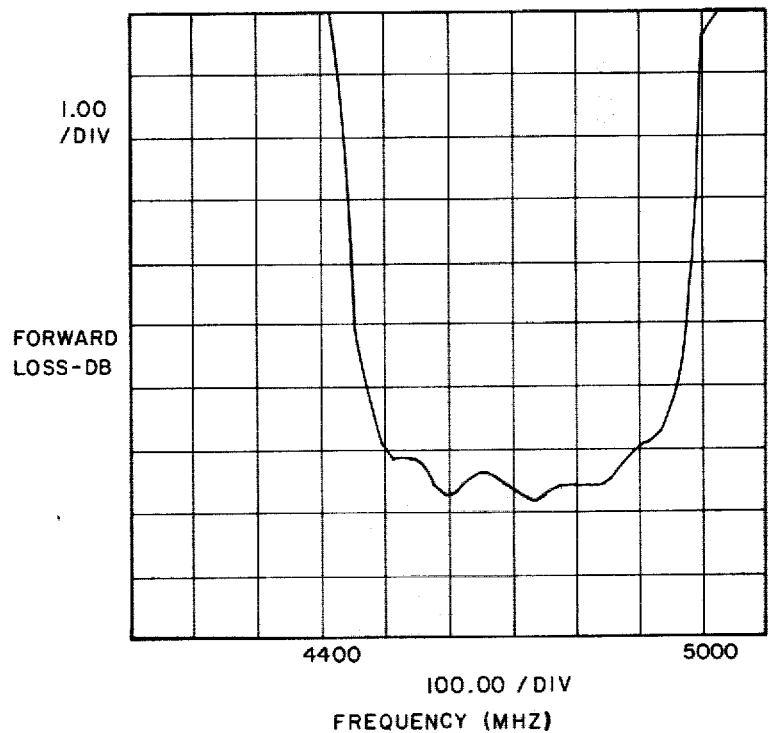
FIG. 6 is a graph of frequency response for the band-pass filter of FIG. 1.

In FIG. 1 the filter 44 is a bandpass filter and the bandwidth of the microwave radiometer is basically determined by the bandpass characteristics of this filter. The filter is disposed after the first stage of RF amplification to minimize the impact of the insertion loss of the filter on the overall system performance. The filter characteristics are chosen to minimize possible interference due to nearby microwave communications or radar bands. FIG. 6 shows the filter characteristics. The filter is preferably an 8-section bandpass filter constructed in stripline. The pass band loss is less than 3 dB and the bandwidth is approximately 500 MHz.

As indicated in FIG. 1, there are basically two loads provided, a base load 40 and a reference load 42. The load design is coaxial, employing a stainless steel RF connector to provide thermal isolation betwen the load and the remainder of the system. The coaxial termination is contained within an insulated housing and utilizes an integrated heater and proportional control to maintain constant temperature. The absolute temperature of both the base and the reference loads is monitored and displayed on a digital temperature indicator (not shown).

The calibration circuit comprises a precision, solid state, noise source having an excess noise ratio, ENR of 33 dB. This allows noise to be injected into the receiver front end via the high isolation mechanical calibration switch. The output level of the noise source is reduced through the use of a precision calibrated pad (43.3 dB). This calibration circuit is shown in FIG. 1 as including a fixed attenuator 38 and the noise diode 36.

The temperature sensitivity of the noise diode is less than 0.01 dB/°C.

The apparent output noise temperature, $T_{NO}$, at the SPDT switch is $$T_{NO} = \frac{\epsilon T_1}{L} + \left(1 - \frac{1}{L}\right) T_2, °K.$$

where $T_1$ = temperature, ambient, of the source; namely, $273.13° + 22.25°$ or $295.38°$ K.
  $T_2$ = temperature of component in lossy path; namely, $295.38°$ C.
  $\epsilon$ = emissivity or, in this case, excess noise ratio (ENR) of the noise source (33 dB corresponds to a ratio of 1995)
  $L$ = attenuation expressed as a power ratio (43.3 dB corresponds to a ratio of 21,380);

therefore, $$T_{NO} = \frac{(1995)(295.38)}{21,380} + 295.38, \text{ or } 322.9° \text{ K}.$$

thus providing a 12.76° differential with respect to the base load of 310° K.

The lock-in amplifier 50 shown in FIG. 1 is one made by Princeton Applied Research, Model No. 5101. This amplifier enables the accurate measurement of signals contaminated by broadband noise, power line pickup, frequency drift or other sources of interference. It accomplishes this by means of an extremely narrow band detector which has the center of its pass band locked to the frequency of the signal to be measured. Because of the frequency lock and narrow bandwidth, large improvements in signal-to-noise ratio are achieved. This allows the signal of interest to be accurately measured, even in situations where it is completely masked by noise. In addition, the lock-in amplifier 50 provides the synchronous function associated with the Dicke switch; i.e., the unit supplies the 100 Hz reference clock frequency to drive the ferrite switch driver.

The system is provided, of course, with a power supply comprising three 12-volt, 50 amp. maintenance free, lead-acid batteries in series, fused at 10 amps per battery. The outputs from the battery assembly include 12, 24, and 36 volts. These voltages are appropriately applied to the receiver, lock-in amplifier and transmitter. There may also be provided a voltage converter and regulator. Status indicators may be employed for indicating operating voltages. The main operating switch may have three positions including an on position, an off position and a "charged" position. In the charged mode, a meter is used to monitor the charge current to the batteries which is limited to approximately 6 amps. With a 3-9 amp-hour discharge rate (a normal 8 hour operate mode), the recharge cycle is approximately 10-12 hours (overnight).

The microwave transmitter embodied in the system of this invention is shown in FIG. 2. This is an L-band transmitter operating at a frequency of 1.6 GHz. The transmitter includes a 1.6 GHz, 30 W, solid state source 60 which couples to an RF power amplifier, filter, and microwave reflectometer. There are two series connected filters 66 and 68 which are low-pass filters connected in series for providing 120 dB of attenuation at the third harmonic. The third harmonic of the 1.6 GHz source is 4.8 GHz, which is within the radiometer passband. It is intended that the microwave transmitter operates simultaneously with the microwave radiometer to provide localized heating of subsurface tissue, while simultaneously monitoring the temperature with the radiometer described previously. The reflectometer employed in the transmitter of FIG. 2 allows determination of both the reflected and incident power levels. The detector 70 measures the incident level while the detector 72 measures the reflected level. FIG. 2 also shows the output terminal 74 which is the RF output coupling to the applicator.

Figure 7:
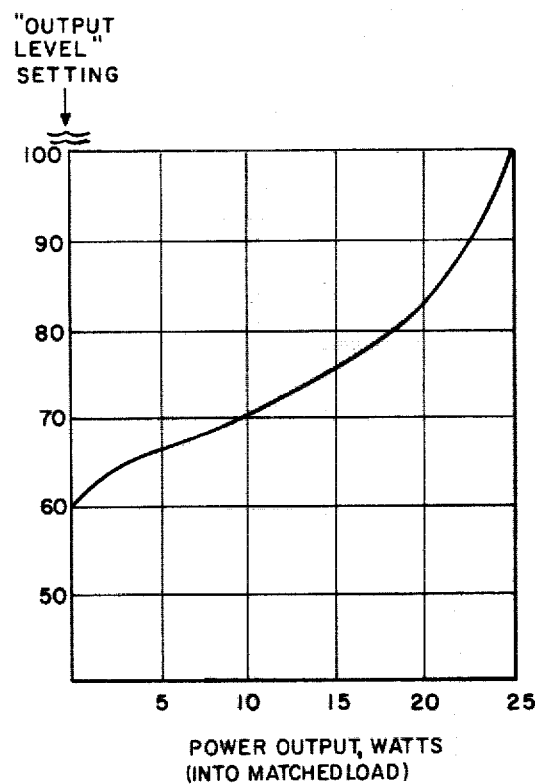
FIG. 7 is a graph of transmitter output level associated with the transmitter of FIG. 2.

The output power level from the transmitter of FIG. 2 is adjustable from 0 to 25 watts (measured at the input to the L-band antenna) and, therefore, includes all microwave circuit and coaxial cable losses. FIG. 7 illustrates the approximate power input plotted as a function of "output level" control setting. This measurement is made into a matched load and, therefore, to be more accurate is reduced according to the load mismatch. A 2.1 load VSWR, for example, correspnds to a 10% power reflection. For an "output level" setting of 70 which corresponds to 10 watts (per FIG. 7), therefore, there are actually 9 watts of incident power with 10% or 1 watt reflected. The reflected energy is terminated in the load associated with the second ferrite isolator 64.

The VSWR (voltage standing wave ratio) is obtained from the following expression:

$$VSWR, r = \frac{P_F + P_R}{P_F - P_R}$$

where $P_R$ and $P_F$ are obtained from the heater efficiency meters "Reflected" and "Forward" respectively.

The ratio of the reflected power, $P_r$, to the incident power, $P_i$, is determined as follows:

$$\frac{P_r}{P_i} = \left(\frac{r-1}{r+1}\right)^2$$

where the total power generated is equal to $P_r + P_i$.

The filter/reflectometer 71 shown in FIG. 2 is a microwave integrated circuit such as one by Microwave Associates Model No. MA-56823. This and other parts are identified in the enclosed Table II which shows the primary elements of the transmitter of FIG. 2, their part number and a brief description of their function or purpose.

TABLE II

| ITEM | PART NO. | |
|---|---|---|
| 1.6 GHz SOURCE | MA-56826 | THE ENTIRE ASSEMBLY FORMS THE 1.6 GHz SOLID STATE 30W SOURCE. |
| RF POWER AMPLIFIER | MA-56829 | THE OUTPUT LEVEL IS ELECTRONICALLY VARIABLE. |
| ISOLATOR - FIRST | MA-56827 | COAXIAL FERRITE ISOLATOR - PROVIDES INTERSTATE ISOLATION BETWEEN FIRST AND SECOND RF AMPLIFIERS, 0.2 dB LOSS, 20 dB MINIMUM ISOLATION |
| ISOLATOR - SECOND | MA-56822 | COAXIAL FERRITE ISOLATOR - PROVIDES ISOLATION BETWEEN THE SOLID STATE SOURCE AND THE EXTERNAL LOAD |
| FILTER | MA-56824 | LOW PASS FILTER - PROVIDES THIRD HARMONIC REJECTION OF GREATER THAN 60 dB. |
| FILTER/ REFLECTOMATER ASSEMBLY | MA-56823 | LOW PASS FILTER - PROVIDES ADDITIONAL 60 dB THIRD HARMONIC REJECTION. COMBUSTION OF DIRECTIONAL COUPLERS AND DETECTOR ALLOWS MEASUREMENT OF FORWARD AND REVERSE POWER. |

The filter/reflectometer assembly 71 is depicted as having four ports including an input port 1 and an output port 2. At a frequency of 1.6 GHz, the insertion loss from Port 1 to 2 is 0.33 dB, the VSWR of Port 1 and 2 is less than 1.15. The coupling between Ports 1 and 4 and Ports 2 and 3 is approximately 40 dB. The coupler associated with Port 4 is, therefore, used to measure the reflected power, whereas the coupler associated with Port 3 is used to measure the incident power. The directivity of the two couplers is 28 and 16 dB respectively. Matched coaxial detectors (HP Model 8472B) are mated to Ports 3 and 4, the output of which is applied to the current meters for registering reflected and incident power levels. These meters are not shown in the schematic of FIG. 2.

As previously mentioned the low pass filters 66 and 68 provide third harmonic rejection. The attenuation due to the low pass filtering is greater than 60 dB at 4.8 GHz.

As mentioned previously, there is a heater 24 depicted in FIG. 5 as used for maintaining the dual mode antenna 10 at a constant temperature close to the human body temperature. When the system is in its charged mode of operation the heater 24 is maintained operating as are heaters associated with the reference load and the base load. This eliminates any need for an extensive "warm-up."

The lock-in amplifier 50 may have associated therewith certain controls and a meter. One of the controls is a signal sensitivity control. The next control is an offset control which allows zeroing of the meter. Another control that may be provided is a time constant pre-filter control which can be normally set in the one or three second position. A further control is a reference control. The last control is a mode selector control.

With regard to the transmitter of FIG. 2, there are controls associated therewith. These controls include an on-off switch which is used to activate the transmitter and a ten-turn control to adjust the output level. A control knob allows adjustment of one of the meters associated with the transmitter to full scale to monitor the applicator efficiency. The ratio between the two meters associated with the transmitter indicates the heater efficiency.

The dual mode microwave system depicted in FIGS. 4 and 5 includes two antennae 10, 12, heater 24, and a proportional thermostat not shown in that drawing which is cabled back to the receiver and transmitter. The two antennae are a transmitter antenna or heat antenna and a receiver antenna. The heater 24 is self-contained within the applicator body and is used to maintain the applicator at body temperature. There is associated with the heater a thermostat, as mentioned, for maintaining the proper temperature at the applicator. FIG. 5 shows schematically the connection of the thermostat between the heater 24 and an electrical source.

The waveguide constructions, such as shown in FIGS. 4 and 5, are preferably of a ceramic material such as aluminum oxide with the outer boundaries of the waveguide being formed by means of a metallic plating on the ceramic. This plating may be of nickel, copper or gold. This arrangement is depicted in FIG. 4 by a small cut-out portion showing the plating and the ceramic material. With the L-band waveguide construction being essentially fitted within the C-band waveguide construction, only a single plating is necessary between the components.

One of the advantages of the present invention is that with this system, integrity is maintained between the applicator and the aperture without interference occurring between transmitted heating signals and detected signals. In this way the microwave heating signal can be maintained essentially "on" at all times without any necessity for interruption of this signal for detecting temperature.

The two frequencies that have been selected herein, one in C-band and one in L-band have not been selected indiscriminately but rather have been selected based upon such factors as emissivity, spacial resolution and transmission characteristics. For example, the microwave heating frequency has preferably been selected lower than the radiometer frequency as the lower heating frequency provides a deeper penetration of microwave heating. On the other hand, the radiometer frequency is selected higher preferably because at the higher frequency there is an increased resolution which is desired for detecting, in particular, a small temperature differential.

What is claimed is:

1. A microwave system for the detection of cancer employing non-invasive techniques, comprising:
    a microwave transmitter,
    an applicator including a waveguide construction and adapted to be maintained in contact with a human body site,
    means coupling the microwave transmitter to the applicator for establishing at the applicator a heating temperature greater than the normal human body temperature,
    means defining a sensing aperture including a second waveguide construction also adapted to be maintained in contact with a human body site,
    a microwave radiometer,
    means coupling the sensing aperture to the microwave radiometer whereby the radiometer is for sensing at a resolution of fractions of a centigrade degree,
    and housing means for commonly supporting at least said applicator and aperture in close proximity to each other whereby the localized heating enhances differential heating associated with the thermal characteristics of tumors to enable early detection,
    said housing means including means for permitting an operator to hold the housing means to enable contact under manual control with the human body,
    said applicator waveguide construction comprising a ridged waveguide having means defining a ridge,
    said aperture waveguide construction comprising a rectangular waveguide disposed in the ridge of the applicator waveguide construction.

2. A microwave system as set forth in claim 1 wherein said microwave transmitter comprises an L-band source, power amplifier and filter means.

3. A microwave system as set forth in claim 2 wherein said filter means is for filtering harmonics of the source frequency.

4. A microwave system as set forth in claim 3 including output reflectometer means.

5. A microwave system as set forth in claim 1 wherein said microwave transmitter and microwave radiometer operate at different frequencies.

6. A microwave system as set forth in claim 5 wherein the output heating frequency associated with the microwave transmitter is less than the detection pass band frequency associated with the microwave radiometer.

7. A microwave system as set forth in claim 6 wherein the transmitter frequency is in L-band and the radiometer frequency is in C-band.

8. A microwave system as set forth in claim 7 wherein the transmitter frequency is on the order of 1.6 GHz and the radiometer frequency is on the order of 4.7 GHz.

9. A microwave system as set forth in claim 1 wherein the microwave radiometer comprises square law detection means and filter means having a pass band outside of the frequency range of the transmitter.

10. A microwave system as set forth in claim 9 including a Dicke switch means and a reference load with the Dicke switch means coupling the square law detection means or the reference load to the filter means.

11. A microwave system as set forth in claim 10 including input calibration means comprising switch means, and a calibration circuit with the switch means switchable between an input signal and the calibration circuit.

12. A microwave system as set forth in claim 1 wherein said ridged waveguide is dielectric loaded.

13. A microwave system as set forth in claim 1 wherein said ridged waveguide has a single ridge.

14. A microwave system as set forth in claim 1 wherein the waveguide is a ceramic guide plated with a conductive metal.

15. A microwave system as set forth in claim 1 comprising heater means disposed intermediate the ridged and rectangular waveguides.

16. A microwave system as set forth in claim 15 wherein said heater means is in a sheet and maintains the applicator outer contact surface at about body temperature.

17. A microwave system as set forth in claim 1 wherein said housing means comprises an insulated housing having a handle for support thereof.

18. A microwave system as set forth in claim 1 wherein said housing means comprises an insulated housing having a relatively flat face formed at least in part by the terminating end of the applicator and aperture.

19. A microwave system as set forth in claim 18 including registration marks on the housing to properly align the housing with a body site.

* * * * *